US011826326B2

(12) United States Patent
Lin et al.

(10) Patent No.: US 11,826,326 B2
(45) Date of Patent: Nov. 28, 2023

(54) BENZOIC ACID OR A SALT AND DERIVATIVE THEREOF FOR USE IN PREVENTING OR TREATING DEPRESSION

(71) Applicants: Chieh-Hsin Lin, Kaohsiung (TW); Hsien-Yuan Lane, Taichung (TW); EXCELSIOR PHARMATECH LABS, Taipei (TW)

(72) Inventors: Chieh-Hsin Lin, Kaohsiung (TW); Hsien-Yuan Lane, Taichung (TW)

(73) Assignees: EXCELSIOR PHARMATECH LABS, Taipei (TW); Hsien-Yuan Lane, Taichung (TW); Chieh-Hsin Lin, Kaohsiung (TW)

( * ) Notice: Subject to any disclaimer, the term of this patent is extended or adjusted under 35 U.S.C. 154(b) by 554 days.

(21) Appl. No.: 16/766,314

(22) PCT Filed: Nov. 22, 2018

(86) PCT No.: PCT/MY2018/000035
§ 371 (c)(1),
(2) Date: May 22, 2020

(87) PCT Pub. No.: WO2019/103597
PCT Pub. Date: May 31, 2019

(65) Prior Publication Data
US 2020/0360321 A1 Nov. 19, 2020

Related U.S. Application Data

(60) Provisional application No. 62/589,933, filed on Nov. 22, 2017.

(51) Int. Cl.
*A61K 31/192* (2006.01)
*A61K 45/06* (2006.01)
*A61P 25/24* (2006.01)
*A61N 1/36* (2006.01)
*A61N 1/38* (2006.01)
*A61N 2/00* (2006.01)
*A61N 5/06* (2006.01)

(52) U.S. Cl.
CPC ............ *A61K 31/192* (2013.01); *A61K 45/06* (2013.01); *A61P 25/24* (2018.01); *A61N 1/36025* (2013.01); *A61N 1/36053* (2013.01); *A61N 1/36096* (2013.01); *A61N 1/38* (2013.01); *A61N 2/002* (2013.01); *A61N 2/006* (2013.01); *A61N 5/0618* (2013.01)

(58) Field of Classification Search
CPC ....... A61K 31/192; A61K 45/06; A61P 25/24; A61N 1/36025; A61N 1/36053; A61N 1/36096; A61N 1/38; A61N 5/0618; A61N 2/002; A61N 2/006
USPC .......................................................... 514/568
See application file for complete search history.

(56) References Cited

FOREIGN PATENT DOCUMENTS

| CN | 108553456 | 9/2018 |
|---|---|---|
| WO | 2010/085452 | 7/2010 |
| WO | 2015/109215 | 7/2015 |
| WO | 2015/147742 | 10/2015 |
| WO | 2017/215593 | 12/2017 |
| WO | 2018/077157 | 5/2018 |

OTHER PUBLICATIONS

Keller et al., A Comparison of Nefazodone, the Cognitive Behavioral-Analysis System of Psychotherapy, and Their Combination for the Treatment of Chronic Depression, 2000, The New England Journal of Medicine, vol. 342, No. 20, pp. 1462-1470 (Year: 2000).*
International Search Report and Written Opinion for International Application No. PCT/MY2018/000035 dated Feb. 12, 2019, 14 pages.
Lai, et al. "Clinical and Cerebral Volumetric Effects of Sodium Benzoate, a d-Amino Acid Oxidase Inhibitor, in a Drug-Naive Patient with Major Depression", Biological Psychiatry, 2012, vol. 71, Issue 4, pp. e9-e10, published Feb. 15, 2012 <URL: https://www.biologicalpsychiatryjournal.com/article/S0006-3223(11)01093-6/fulltext>.
Lai, "Sodium Benzoate, a D-Amino Acid Oxidase Inhibitor, Increased Volumes of Thalamus, Amygdala, and Brainstem in a Drug-Naive Patient with Major Depression", The Journal of Neuropsychiatry and Clinical Neurosciences, 2013, vol. 25, Issue 1, pp. E50-E51, published Jan. 1, 2013 <URL: https://neuro.psychiatryonline.org/doi/full/10.1176/appi.neuropsych.12030056>.

* cited by examiner

*Primary Examiner* — Kristin A Vajda
(74) *Attorney, Agent, or Firm* — AMIN, TUROCY & WATSON, LLP

(57) ABSTRACT

The present disclosure provides a method of preventing or treating depression in a subject in need thereof, including administering to the subject an effective amount of benzoic acid, or a salt or derivative thereof. Also provided is a composition for use in preventing or treating depression in a subject in need thereof.

12 Claims, No Drawings

BENZOIC ACID OR A SALT AND DERIVATIVE THEREOF FOR USE IN PREVENTING OR TREATING DEPRESSION

BACKGROUND

1. Technical Field

The present disclosure relates to prophylaxis or treatment of depression, particularly to methods for preventing or treating depression by administering to a subject in need thereof a composition comprising benzoic acid or a salt and derivative thereof. Also related is a composition for use in preventing or treating depression in a subject in need thereof.

2. Description of Associated Art

Major depressive disorder (MDD) is a severe and common mental disorder. MDD is the leading cause of suicide (Harwood, Hawton et al. 2001; Waern, Runeson et al. 2002) and is associated with disability and pain (Ohayon and Schatzberg 2003), cognitive deficits (Steffens, Skoog et al. 2000; Mecocci, Cherubini et al. 2004), and unnecessary use of medical resources and social welfare (VanValkenburg, Akiskal et al. 1984; Saravay and Lavin 1994), especially in the elderly population. Due to its excess morbidity and mortality (Miu and Chan 2010), depression has become a major public health problem which needs to be taken seriously by the government and the public.

MDD is a complex and multi-factorial disorder, whose etiology cannot be explained by a single gene or a single environmental factor (Dagyte, Den Boer et al. 2011). Most of the current antidepressants are based upon the monoamine (e.g., serotonin, norepinephrine, and dopamine) hypothesis (Charney 1998). However, it usually takes more than 3 to 4 weeks for the onset of efficacy, and about 30-60% of patients with MDD fail to recover (Riihimaki, Vuorilehto et al. 2014; Keller, Lavori et al. 1992), implying that the monoamine hypothesis cannot fully explain the etiology of depression. A study published on Lancet compared the efficacy of sertraline, mirtazapine, and placebo for the treatment of depression in patients with dementia. The result showed that the antidepressant groups (i.e., sertraline and mirtazapine) did not differ from the placebo group in the reduction of depression scores (Banerjee, Hellier et al. 2011); furthermore, the antidepressant groups had significantly more adverse reactions when compared to the placebo group (42% vs. 26%). The negative results of the study with large sample size and long follow-up duration suggested that the use of antidepressants for first-line treatment of depression in Alzheimer's disease should be reconsidered. Many patients have significant side effects after treatment with antidepressants, such as gastrointestinal discomfort, cardiac toxicity, anticholinergic effects, sedation or agitation, insomnia and hyponatremia which hamper the motivation for treatment and medication adherence. Hence, there is a great need to develop novel therapies with better efficacy and safer adverse effect profile via mechanisms other than monoamine theory for patients with MDD.

Glutamate is the most abundant amino acid neurotransmitter in mammalian brain. N-methyl-D-aspartate (NMDA) receptor, a subtype of ionotropic glutamate receptor, plays an important role in neurocognition and neurotoxicity. Depression may have complex neural substrates in that both up- and down-regulation of NMDA function are involved. NMDA receptors are widely distributed in corticolimbic circuitries, and it is not surprising that a complex behavioral disorder like depression involves multiple NMDA receptor circuitries that may have opposite directions of regulation.

NMDA hypofunction might be implicated in the pathophysiology of depression. NMDA receptor 1 and 2A subunit expression is decreased in post-mortem brains of subjects with major depression (Beneyto and Meador-Woodruff 2008) and NMDA receptor binding is reduced in suicide victims (Nowak, Ordway et al. 1995). Avenues for NMDA enhancement represent a novel therapeutic approach for the treatment of depression.

D-amino acid oxidase (DAAO) is a flavoenzyme of peroxisomes existing in the brain, kidney and liver of mammals which is responsible for degrading D-serine, D-alanine, and other D-amino acids (Fukui and Miyake 1992; Vanoni, Cosma et al. 1997). A way to enhance NMDA function is via inhibiting DAAO activity. Benzoic acid and sodium benzoate can inhibit DAAO activity, thereby raising synaptic concentrations of D-serine and other D-amino acids (Bartlett 1948; Van den Berghe-Snorek and Stankovich 1985). Benzoic acid occurs naturally in many plants and in animals. It is therefore a natural constituent of many foods, including milk products (IPCS 1993). Benzoic acid and sodium benzoate are also legal food additives in USA (Joint FAO/WHO Expert Committee on Food Additives. 1965, 1973), Taiwan (Department of Health), and World Health Organization (IPCS 1993), and are widely used in manufacturing fruit jelly, butter, soy-bean sauce, processed meat, etc.

To test whether the benzoic acid or the salts and derivatives thereof are beneficial for depression, it has been conducted in the trials of the present disclosure to examine the efficacy and safety in patients with depression.

SUMMARY

In view of the foregoing, the present disclosure provides a method of preventing or treating depression comprising administering to a subject in need thereof an effective amount of benzoic acid, or a salt or derivative thereof and a pharmaceutically acceptable excipient.

In one embodiment of the present disclosure, the subject is diagnosed with dementia. In one embodiment, the dementia includes Alzheimer's disease, vascular dementia, Lewy body dementia, frontotemporal dementia, mixed dementia, dementia due to medical conditions or substance use, normal pressure hydrocephalus, Parkinson's disease dementia, syphilis, or Creutzfeldt-Jakob disease, but not limited thereto.

In one embodiment of the present disclosure, the benzoic acid salt and derivative thereof is sodium benzoate, potassium benzoate, calcium benzoate, magnesium benzoate, 2-aminobenzoate, 3-aminobenzoate, 4-aminobenzoate, ethyl 4-hydroxybenzoate, sodium ethyl 4-hydroxybenzoate, propyl-4-hydroxybenzoate, sodium propyl-4-hydroxybenzoate, methyl 4-hydroxybenzoate, or sodium 4-hydroxybenzoate, but not limited thereto.

In another embodiment of the present disclosure, the benzoic acid salt is sodium benzoate.

In one embodiment of the present disclosure, the depression includes, but not limited to, major depressive disorder (MDD), geriatric depression, elderly depression or late-life depression.

In one embodiment of the present disclosure, the benzoic acid or the salt and derivative thereof is administered to a subject in need thereof in an amount of from 100 mg/day to 2500 mg/day, from 200 mg/day to 2000 mg/day, from 250 mg/day to 1500 mg/day, from 250 mg/day to 1000 mg/day, from 500 mg/day to 1000 mg/day, or from 600 mg/day to 800 mg/day.

In one embodiment of the present disclosure, the pharmaceutically acceptable excipient is selected from the group consisting of a filler, a binder, a preservative, a disintegrating agent, a lubricant, a suspending agent, a wetting agent, a solvent, a surfactant, an acid, a flavoring agent, polyethylene glycol (PEG), alkylene glycol, sebacic acid, dimethyl sulfoxide, an alcohol, and any combination thereof.

In one embodiment of the present disclosure, the benzoic acid or the salt and derivative thereof serves as a sole active ingredient for preventing or treating the depression in the composition, or the benzoic acid or the salt and derivative thereof is in combination with an additional active ingredient for preventing or treating the depression. In one embodiment, the additional active ingredient is selected from the group consisting of duloxetine, levomilnacipran, venlafaxine, desvenlafaxine, citalopram, escitalopram, fluoxetine, fluvoxamine, paroxetine, sertraline, amitriptyline, amoxapine, clomipramine, desipramine, doxepin, imipramine, nortriptyline, protriptyline, trimipramine, maprotiline, bupropion, vilazodone, nefazodone, trazodone, vortioxetine, isocarboxazid, phenelzine, selegiline, tranylcypromine, mirtazapine, olanzapine, quetiapine, aripiprazole, sulpiride, flupentixol, melitracen, agomelatine, moclobemide, St. John's wort, S-adenosyl-L-methionine, and any combination thereof, but not limited thereto.

In one embodiment of the present disclosure, administration of the benzoic acid or the salt and derivative thereof is combined with an additional therapy for preventing or treating the depression. In one embodiment, the additional therapy includes, but not limited to, psychotherapy, electroconvulsive therapy (ECT), brain stimulation therapy, light therapy and any combination thereof. In one embodiment, the brain stimulation therapy is deep brain stimulation, invasive vagus nerve stimulation, transcranial magnetic stimulation, transcranial direct current stimulation, transcranial alternating current stimulation, electroconvulsive treatment, magnetic seizure therapy, cranial electrostimulation, or non-invasive vagus nerve stimulation.

DETAILED DESCRIPTION OF THE EMBODIMENTS

The following embodiments are used to exemplify the present disclosure. A person of ordinary skill in the art can conceive the other advantages of the present disclosure, based on the specification of the present disclosure. The present disclosure can also be implemented or applied as described in different embodiments. It is possible to modify and/or alter the examples for carrying out this disclosure without contravening their spirit and scope, for different aspects and applications.

All terms including descriptive or technical terms which are used herein should be construed as having meanings that are obvious to one of ordinary skill in the art. However, the terms may have different meanings according to an intention of one of ordinary skill in the art, case precedents, or the appearance of new technologies. Also, some terms may be arbitrarily selected by the applicant, and in this case, the meaning of the selected terms will be described in detail in the detailed descriptions of the present disclosure. Thus, the terms used herein have to be defined based on the meaning of the terms together with the descriptions throughout the specification.

Also, when a part "includes" or "comprises" a component or a step, unless there is a particular description contrary thereto, the part can further include other components or other steps, not excluding the others.

It is further noted that, as used in this specification, the singular forms "a," "an," and "the" include plural referents unless expressly and unequivocally limited to one referent. The term "or" is used interchangeably with the term "and/or" unless the context clearly indicates otherwise.

The present disclosure provides a method of preventing or treating depression such as MDD in a subject suffering from depression or MDD. In some embodiments of the present disclosure, the subject has been clinically diagnosed with depression or a depression-related mood disorder such as MDD. As used herein, the term "depression" refers to a common mental disorder characterized by a pervasive low mood, loss of interest or pleasure in usual activities, feelings of guilt or low self-worth, disturbed sleep or appetite, low energy, and poor concentration. Depression can lead to a variety of emotional and physical problems and can decrease a person's ability to function at work and at home. At its worst, depression can lead to suicide. The term "depression" also covers depressive disorders, such as mood disorder, major, dysthymic disorder, and MDD (commonly called major depression or clinical depression). A person with MDD has at least two weeks of depressed mood or a loss of interest or pleasure in nearly all activities.

In some embodiments of the present disclosure, the method comprises administering an effective amount of benzoic acid, or a salt or derivative thereof to the subject. In some embodiments of the present disclosure, the effective amount of the benzoic acid, or the salt or derivative thereof may range from 100 mg/day to 2500 mg/day, such as 200 mg/day to 2000 mg/day, 250 mg/day to 1500 mg/day, 250 mg/day to 1000 mg/day, 500 mg/day to 1000 mg/day, 500 mg/day to 900 mg/day, 600 mg/day to 800 mg/day, or about 900 mg/day, about 775 mg/day, about 500 mg/day, or about 250 mg/day. In other embodiments of the present disclosure, the effective amount of the benzoic acid, or the salt or derivative thereof is about 250 mg/day, about 500 mg/day, about 750 mg/day, about 1000 mg/day, about 1250 mg/day, or about 1500 mg/day. In some embodiments of the present disclosure, the lower limit of the effective amount of the benzoic acid, or the salt or derivative thereof is 100 mg/day, 200 mg/day, 250 mg/day, 500 mg/day, 600 mg/day, 750 mg/day, 775 mg/day, 800 mg/day, 900 mg/day, 1000 mg/day, 1250 mg/day, 1500 mg/day or 2000 mg/day, and the upper limit of the effective amount of the benzoic acid, or the salt and derivative thereof is 2500 mg/day, 2000 mg/day, 1500 mg/day, 1250 mg/day, 1000 mg/day, 900 mg/day, 800 mg/day, 775 mg/day, 750 mg/day, 600 mg/day, 500 mg/day, 250 mg/day or 200 mg/day.

In some embodiments of the present disclosure, the benzoic acid, or the salt or derivative thereof administered to the subject is contained in a pharmaceutical composition. The pharmaceutical composition of the present disclosure comprises benzoic acid, or a salt or derivative thereof and a pharmaceutically acceptable excipient thereof. In an embodiment, the composition of the present disclosure is formulated in a form suitable for oral administration, and thus the composition may be administered to the subject by oral delivery. Alternatively, the composition may be formulated in a form of dry powder, a tablet, a lozenge, a capsule, granule, or a pill. The pharmaceutically acceptable excipient includes, but is not limited to, a filler, a binder, a preservative, a disintegrating agent, a lubricant, a suspending agent, a wetting agent, a solvent, a surfactant, an acid, a flavoring agent, polyethylene glycol (PEG), alkylene glycol, sebacic acid, dimethyl sulfoxide, an alcohol, or any combination thereof.

In some embodiments of the present disclosure, the administration of the composition comprising benzoic acid, or a salt or derivative thereof may be conducted, for example, once per day, twice per day, 3 times per day, or 4 times per day. In some embodiments of the present disclosure, the administration of benzoic acid, or a salt or derivative thereof is daily over at least 4 weeks. In some embodiments of the present disclosure, the administration of benzoic acid or a salt and derivative thereof is daily for 8 weeks.

In some embodiments of the present disclosure, the composition may be administered to the subject in a period sufficient to prevent or treat depression. The sufficient period may depend on the species, gender, body weight or age of the subject, the stage, symptom or severity of the disease, and the routes, timing or frequency of the administration. In some embodiments of the present disclosure, the administration of the composition is daily over at least one month. For example, the period of administration of the composition may last for 1, 2, 3, 4, or 6 months, or 1, 2, 3 or 4 years, or even longer, as long as no side effect occurs during the treatment period. In the exemplary embodiments of the present disclosure, the period may be in a range of from 4 weeks to 2 years. In another embodiment, the period ranges from 2 months to 12 months. In yet another embodiment, the administration of the benzoic acid or the salt and derivative thereof is daily for 12 weeks.

The pharmaceutical composition of the present disclosure may only comprise the benzoic acid or the salt and derivative thereof as an active ingredient for preventing or treating depression. In other words, the benzoic acid or the salt and derivative thereof serves as the only active ingredient for the depression disorder in the composition. In this embodiment, the present disclosure provides a safe and effective therapy for preventing or treating depression by the use of the benzoic acid or the salt and derivative thereof alone as the active ingredient.

Alternatively, in another embodiment, the composition may be administered to a subject in combination with another active ingredient unless the effect of the present disclosure is inhibited. The benzoic acid or the salt and derivative thereof and another active ingredient may be provided in a single composition or in separate compositions. Examples of such compositions may include sodium benzoate, alogliptin benzoate, betamethasone benzoate, benzyl benzoate, metformin hydrochloride, pioglitazone hydrochloride, rizatriptan benzoate, sodium phenylacetate, pioglitazone hydrochloride, and any combination thereof.

In an embodiment, the pharmaceutical compositions of the present disclosure are prepared in suitable dosage forms comprising an effective amount of the pharmaceutical composition of the present disclosure.

Examples of the suitable dosage forms include, but are not limited to, tablets, capsules, coated tablets, granules, solutions and syrups for oral administration; medicated plasters, pastes, creams and ointments for transdermal administration; suppositories for rectal administration; and sterile solutions for administration via the injection or aerosol route.

Other examples of suitable dosage forms include, but are not limited to, those with sustained release or based on liposomes for administration via either the oral or injection route.

The dosage forms may also contain other conventional ingredients, for instance, preserving agents, stabilizers, surfactants, buffers, osmotic pressure-regulating salts, emulsifiers, sweeteners, colorants, flavorings and the like, but not limited thereto.

In an embodiment, the administration of the benzoic acid or the salt and derivative thereof in the method provided by the present disclosure may be combined with any suitable therapy for depression.

As used herein, when a number or a range is recited, a person having ordinary skill in the art understands that it intends to encompass an appropriate, reasonable range for the particular field related to the disclosure.

By at least 100 mg to 2500 mg, it means that all integer unit amounts within the range are specifically disclosed as part of the disclosure. Thus, 100, 101, 102, . . . 250, 251, 252, . . . 1000, 1001, 1002, . . . 2497, 2498, 2499 and 2500 unit amounts are included as embodiments of the present disclosure.

The term "treating" or "treatment" refers to administration of an effective amount of benzoic acid, or a salt or derivative thereof to a subject in need thereof with the purpose of cure, alleviate, relieve, remedy, or ameliorate the disease, the symptoms thereof, or the predisposition towards it. Such a subject can be identified by a health care professional based on results from any suitable diagnostic method.

The phrase "an effective amount" refers to the amount of an active ingredient that is required to confer a therapeutic effect on the treated subject. Effective doses will vary, as recognized by those skilled in the art, depending on routes of administration, excipient usage, and the possibility of co-usage with other therapeutic treatment.

In certain embodiments of the present disclosure, the method involves the use of benzoic acid, a benzoic acid salt, or a derivative thereof, which can be selected from the group consisting of benzoic acid, sodium benzoate, potassium benzoate, calcium benzoate, magnesium benzoate, 2-aminobenzoate, 3-aminobenzoate, 4-aminobenzoate, ethyl 4-hydroxybenzoate, sodium ethyl 4-hydroxybenzoate, propyl 4-hydroxybenzoate, sodium propyl-4-hydroxybenzoate, methyl 4-hydroxybenzoate, and sodium 4-hydroxybenzoate, but not limited thereto.

In certain embodiments of the present disclosure, the benzoic acid or the salt and derivative thereof is administered in an oral dosage form.

Many examples have been used to illustrate the present disclosure. The examples below should not be taken as a limit to the scope of the present disclosure.

EXAMPLE

The present disclosure examined the efficacy and safety of sodium benzoate, a DAAO inhibitor, for the treatment of MDD.

It was conducted a randomized, double-blind, placebo-controlled trial in Taiwan. Forty patients with MDD were treated with sodium benzoate or placebo for 8 weeks, twenty patients in each group. At the baseline and at the end of week 2, 4, 6 and 8, the assessments of 17-Item Hamilton rating scale for depression (HAMD-17) (Hamilton 1960), perceived stress scale (PSS), and global assessment of function (GAF) were arranged.

Participants

This study was a pilot eight weeks trial with the aim of examining sodium benzoate for the treatment of MDD. Patients were evaluated by research psychiatrists after a thorough medical and neurological workup. The structured clinical interview for DSM-IV (SCID) (American Psychiatric Association 1994) was conducted for diagnosis, and eligible patients diagnosed with MDD by DSM-IV (American Psychiatric Association 1994b) were recruited. All patients were randomly assigned into two groups, placebo or sodium benzoate (250-1500 mg/day, e.g., 250 mg/day, 500 mg/day, 750 mg/day, 1000 mg/day, 1250 mg/day or 1500 mg/day). The dosage of study drugs was adjusted according to clinical evaluation.

Assessments

The efficacy of sodium benzoate on treatment of MDD was assessed by HAMD-17, PSS and GAF at the end of week 2, 4, 6 and 8.

In addition, the assessments of systemic side effects were examined biweekly by routine physical and neurological examinations and the Udvalg for Kliniske Undersogelser (UKU) side-effects rating scale (Lingjaerde, Ahlfors et al. 1987). The routine laboratory tests, including complete blood count (CBC), biochemistry, urine analysis and electrocardiogram (EKG), were checked at the baseline and at the end of week 8.

Further, clinical assessment of safety was performed every week during the study period by face-to-face or telephone interview. Drop out was determined by research psychiatrists or patients if continuation of the study was regarded obviously more risky than beneficial.

Data Analysis

The data analyses were based on the intent-to-treat principle. The last observation carried forward was used to analyze all available data from the entire sample (i.e., cases with complete and incomplete data). A level of 0.05 (two-sided value) for type I errors was adopted for all analyses for statistical significance. Demographic characteristics, baseline and endpoint symptomatology were compared between two groups by t test (or Mann-Whitney U test) for continuous variables and chi-square test (or Fisher's exact test) for categorical variables.

Results

As shown in Table 1 below, the demographic data and education level were similar among the sodium benzoate group and the placebo group (p>0.05), and the mean dose of sodium benzoate at the endpoint was 775.0±213.1.

TABLE 1

Baseline demographic characteristics of the sodium benzoate group or the placebo treatment group

| | Treatment Groups | | |
|---|---|---|---|
| | Benzoate (n = 20) | Placebo (n = 20) | p Value |
| Gender, female, n (%) | 13 (65.0) | 14 (70.0) | 1.000 [a] |
| Age, year, mean (SD) | 67.9 (7.6) | 68.4 (5.7) | 0.802 [b] |
| Education, year, mean (SD) | 8.2 (5.0) | 8.0 (3.7) | 0.968 [c] |
| Dose at endpoint, mean (SD) | 775.0 (213.1) | NA | |

[a] Fisher's Exact test;
[b] independent t-test;
[c] Mann-Whitney U test;
NA, not associated The assessment results of HAMD-17, GAF and PSS were shown in Table 2 below. It showed that there were no significant differences in the mean±SD scores of HAMD, GAF and PSS between the two groups of patients at week 0 (baseline).

However, for the HAMD-17 scores, it was found that the differences of the mean scores between baseline and that at week 8 for the sodium benzoate group and the placebo group (p=0.011) were 7.5±4.9 and 2.8±6.1, respectively, after treatment for 8 weeks. It could be seen that sodium benzoate provided greater improvement in HAMD-17 scores than the placebo therapy.

In addition, for the HPSS scores, it was found that the differences of the mean scores between baseline and that at week 8 for the sodium benzoate group and the placebo group (p=0.022) were 6.4±9.9 and 0.4±4.6, respectively, after treatment for 8 weeks. It could be seen that sodium benzoate also provided greater improvement in PSS scores than the placebo therapy.

Further, for GAF cores, the differences of the mean scores between baseline and that at week 8 for the sodium benzoate group and the placebo group (p=0.022) were 5.5±6.0 and 1.9±7.7, respectively, after treatment for 8 weeks. It showed that sodium benzoate provided slightly greater improvement than the placebo therapy in GAF cores.

TABLE 2

Assessment results of HAMD-17, GAF and PSS over the 8-week treatment

| Scale | Benzoate Mean ± SD | Placebo Mean ± SD | P Value [a] |
|---|---|---|---|
| HAMD-17 | | | |
| Baseline | 26.7 ± 5.2 | 24.9 ± 5.7 | 0.304 |
| Endpoint | 19.3 ± 6.4 | 22.2 ± 9.7 | 0.270 |
| Difference | −7.5 ± 4.9 | −2.8 ± 6.1 | 0.011 |
| GAF | | | |
| Baseline | 57.4 ± 8.4 | 60.2 ± 6.5 | 0.246 |
| Endpoint | 62.9 ± 9.4 | 62.0 ± 9.6 | 0.778 |
| Difference | 5.5 ± 6.0 | 1.9 ± 7.7 | 0.103 |
| PSS | | | |
| Baseline | 35.2 ± 5.8 | 36.0 ± 4.2 | 0.645 |
| Endpoint | 28.9 ± 10.8 | 35.6 ± 5.2 | 0.019 |
| Difference | −6.4 ± 9.9 | −0.4 ± 4.6 | 0.022 |

[a] independent t-test
Abbreviations: HAMD-17, 17-item Hamilton Rating Scale for Depression; GAF, Global Assessment of Function; PSS, Perceived Stress Scale.

Among the 20 subjects in the treatment group who take sodium benzoate, a 58 years old male has his HAMD-17 score decreased by 20, from 24 to 4, after taking sodium benzoate for 8 weeks. At the same time, the mini-mental state examination (MMSE) score, which is used to evaluate cognitive impairment, has improved from 26 to 30. Another subject from the treatment group, a 77 years old male has seen a HAMD-17 score decreased by 16, from 31 to 15, and also improved MMSE score from 23 to 25. Furthermore, an 80 years old female has a decrease of HAMD-17 score from 26 to 12, and improved cognitive function as shown by an increased MMSE score from 23 to 26. Accordingly, treatment of sodium benzoate improved not only depression in the subjects receiving the treatment, but also their cognitive functions.

Treatment-emergent adverse events were assessed by the UKU side-effects rating scale, and the assessment results showed that the side effect was mild and not warranting medical treatment. They were to be considered as coincidental observations. In addition, the values of routine CBC, biochemistry and EKG tests were all within the normal ranges without a significant change after treatment of sodium benzoate. No dropout was due to side effects. In addition, commonly seen sides effects of anti-depression medication such as nausea, nervousness, restlessness, irregular heart rate, sweating, and digestive tract problems such as constipation, were not observed in the subjects from the treatment group.

The foregoing descriptions of the detailed embodiments are only illustrated to disclose the principle and functions of the present disclosure and do not restrict the scope of the present disclosure. It should be understood to those skilled in the art that all modifications and variations according to the spirit and principle in the disclosure of the present disclosure should fall within the scope of the appended claims. It is intended that the specification and examples are considered as exemplary only, with a true scope of the disclosure being indicated by the following claims.

The references listed below in the disclosure are each incorporated by reference as if they were incorporated individually.

American Psychiatric Association (1994). "Structured Clinical Interview for DSM-IV." American Psychiatric Press: Washington, D.C.
Banerjee, S., J. Hellier, et al. (2011) "Sertraline or mirtazapine for depression in dementia (HTA-SADD): a randomised, multicentre, double-blind, placebo-controlled trial." Lancet 378(9789): 403-411.
Bartlett, G. R. (1948). "The inhibition of d-amino acid oxidase by benzoic acid and various monosubstituted benzoic acid derivatives." J Am Chem Soc 70(3): 1010.
Beneyto, M. and J. H. Meador-Woodruff (2008). "Lamina-specific abnormalities of NMDA receptor-associated postsynaptic protein transcripts in the prefrontal cortex in schizophrenia and bipolar disorder." Neuropsychopharmacology 33(9): 2175-2186.
Charney, D. S. (1998). "Monoamine dysfunction and the pathophysiology and treatment of depression." J Clin Psychiatry 59 Suppl 14: 11-14.
Dagyte, G., J. A. Den Boer, et al. (2011). "The cholinergic system and depression." Behav Brain Res 221(2): 574-582.
Fukui, K. and Y. Miyake (1992). "Molecular cloning and chromosomal localization of a human gene encoding D-amino-acid oxidase." J Biol Chem 267(26): 18631-18638.
Guy, W. (1976). "ECDEU Assessment Manual for Psychopharmacology, revised." US Dept Health, Education, and Welfare publication (ADM) 76-338. Rockville, Md.: National Institute of Mental Health: 217-222.
Hamilton, M. (1960). "A rating scale for depression." J Neurol Neurosurg Psychiatry 23: 56-62.
Harwood, D., K. Hawton, et al. (2001). "Psychiatric disorder and personality factors associated with suicide in older people: a descriptive and case-control study." Int J Geriatr Psychiatry 16(2): 155-165.
IPCS (1993). "International Chemical Safety Card—Benzoic acid and sodium benzoate." Geneva, World Health Organization, International Programme on Chemical Safety (ICSC 0103).
Keller, M. B., P. W. Lavori, et al. (1992). "Time to recovery, chronicity, and levels of psychopathology in major depression. A 5-year prospective follow-up of 431 subjects." Arch Gen Psychiatry 49(10): 809-816.
Lingjaerde, O., U. G. Ahlfors, et al. (1987). "The UKU side effect rating scale. A new comprehensive rating scale for psychotropic drugs and a cross-sectional study of side effects in neuroleptic-treated patients." Acta Psychiatr Scand Suppl 334: 1-100.
Mecocci, P., A. Cherubini, et al. (2004). "Depression in the elderly: new concepts and therapeutic approaches." Aging Clin Exp Res 16(3): 176-189.
Miu, D. K. and C. K. Chan (2010) "Prognostic value of depressive symptoms on mortality, morbidity and nursing home admission in older people." Geriatr Gerontol Int 11(2): 174-179.
Nowak, G., G. A. Ordway, et al. (1995). "Alterations in the N-methyl-D-aspartate (NMDA) receptor complex in the frontal cortex of suicide victims." Brain Res 675(1-2): 157-164.
Ohayon, M. M. and A. F. Schatzberg (2003). "Using chronic pain to predict depressive morbidity in the general population." Arch Gen Psychiatry 60(1): 39-47.
Riihimaki, K. A., M. S. Vuorilehto, et al. (2014) "Five-year outcome of major depressive disorder in primary health care." Psychol Med: 1-11.
Saravay, S. M. and M. Lavin (1994). "Psychiatric comorbidity and length of stay in the general hospital. A critical review of outcome studies." Psychosomatics 35(3): 233-252.
Steffens, D. C., I. Skoog, et al. (2000). "Prevalence of depression and its treatment in an elderly population: the Cache County study." Arch Gen Psychiatry 57(6): 601-607.
Van den Berghe-Snorek, S. and M. T. Stankovich (1985). "Thermodynamic control of D-amino acid oxidase by benzoate binding." J Biol Chem 260(6): 3373-3379.
Vanoni, M. A., A. Cosma, et al. (1997). "Limited proteolysis and X-ray crystallography reveal the origin of substrate specificity and of the rate-limiting product release during oxidation of D-amino acids catalyzed by mammalian D-amino acid oxidase." Biochemistry 36(19): 5624-5632.
VanValkenburg, C., H. S. Akiskal, et al. (1984). "Anxious depressions. Clinical, family history, and naturalistic outcome—comparisons with panic and major depressive disorders." J Affect Disord 6(1): 67-82.
Waern, M., B. S. Runeson, et al. (2002). "Mental disorder in elderly suicides: a case-control study." Am J Psychiatry 159(3): 450-455.

What is claim is:

1. A method for preventing or treating depression and improving cognition in a subject in need thereof, comprising administering a composition comprising an effective amount of benzoic acid, or a salt or derivative thereof, and a pharmaceutically acceptable excipient thereof to the subject, wherein the depression is geriatric depression, late-life depression, or elderly depression.

2. The method according to claim 1, wherein the benzoic acid or the salt and derivative thereof is sodium benzoate, potassium benzoate, calcium benzoate, magnesium benzoate, 2-aminobenzoate, 3-aminobenzoate, 4-aminobenzoate, ethyl 4-hydroxybenzoate, sodium ethyl 4-hydroxybenzoate, propyl-4-hydroxybenzoate, sodium propyl-4-hydroxybenzoate, methyl 4-hydroxybenzoate, or sodium 4-hydroxybenzoate.

3. The method according to claim 1, wherein the benzoic acid salt is sodium benzoate.

4. The method according to claim 1, wherein the benzoic acid or the salt and derivative thereof is administered to the subject in an amount of from 100 mg/day to 2500 mg/day.

5. The method according to claim 4, wherein the benzoic acid or the salt and derivative thereof is administered to the subject in an amount of from 250 mg/day to 1500 mg/day.

6. The method according to claim 5, wherein the benzoic acid or the salt and derivative thereof is administered to the subject in an amount of from 500 mg/day to 1000 mg/day.

7. The method according to claim 1, wherein the pharmaceutically acceptable excipient is selected from the group consisting of a filler, a binder, a preservative, a disintegrating agent, a lubricant, a suspending agent, a wetting agent, a solvent, a surfactant, an acid, a flavoring agent, polyethylene glycol (PEG), alkylene glycol, sebacic acid, dimethyl sulfoxide, an alcohol, and any combination thereof.

8. The method according to claim 1, wherein the benzoic acid or the salt and derivative thereof serves as a sole active ingredient for the depression in the composition.

9. The method according to claim 1, wherein the benzoic acid or the salt and derivative thereof is administered in combination with an additional active ingredient for the depression.

10. The method according to claim 9, wherein the additional active ingredient is selected from the group consisting of duloxetine, levomilnacipran, venlafaxine, desvenlafaxine, citalopram, escitalopram, fluoxetine, fluvoxamine, paroxetine, sertraline, amitriptyline, amoxapine, clomipramine, desipramine, doxepin, imipramine, nortriptyline, protriptyline, trimipramine, maprotiline, bupropion, vilazodone, nefazodone, trazodone, vortioxetine, isocarboxazid, phenelzine, selegiline, tranylcypromine, mirtazapine, olanzapine, quetiapine, aripiprazole, sulpiride, flupentixol, melitracen, agomelatine, moclobemide, St. John's wort, S-adenosyl-L-methionine, and any combination thereof.

11. The method according to claim 1, wherein the benzoic acid or the salt and derivative thereof is administered in combination with an additional therapy for the depression, and wherein the additional therapy is selected from the group consisting of psychotherapy, electroconvulsive therapy (ECT), brain stimulation therapy, light therapy and any combination thereof.

12. The method according to claim 11, wherein the brain stimulation therapy is deep brain stimulation, invasive vagus nerve stimulation, transcranial magnetic stimulation, transcranial direct current stimulation, transcranial alternating current stimulation, electroconvulsive treatment, magnetic seizure therapy, cranial electrostimulation, or non-invasive vagus nerve stimulation.

\* \* \* \* \*